United States Patent [19]

Schmid et al.

[11] Patent Number: 5,541,272
[45] Date of Patent: Jul. 30, 1996

[54] HIGH ACTIVITY ETHYLENE SELECTIVE METALLOCENES

[75] Inventors: Michael Schmid; Helmut G. Alt, both of Bayreuth, Germany; M. Bruce Welch, Bartlesville, Okla.

[73] Assignee: Phillips Petroleum Company, Bartesville, Okla.

[21] Appl. No.: 253,765

[22] Filed: Jun. 3, 1994

[51] Int. Cl.$^6$ ........................................ C08F 4/64
[52] U.S. Cl. .................... 526/160; 502/117; 526/64; 526/352; 526/348.2; 556/51; 556/53
[58] Field of Search ................... 502/103, 109, 502/117, 120, 132; 556/51, 53; 526/160, 351; 585/521, 523, 524

[56] References Cited

U.S. PATENT DOCUMENTS

| | | | |
|---|---|---|---|
| 4,952,540 | 8/1990 | Kioka et al. | 502/9 |
| 5,049,535 | 9/1991 | Resconi et al. | 502/117 |
| 5,120,867 | 6/1992 | Welborn, Jr. | 556/12 |
| 5,126,303 | 6/1992 | Resconi et al. | 502/132 |
| 5,225,092 | 7/1993 | Emert et al. | 252/50 |
| 5,332,706 | 7/1994 | Nowlin et al. | 502/117 |

*Primary Examiner*—Glenn Caldarola
*Attorney, Agent, or Firm*—Edward L. Bowman

[57] ABSTRACT

Unbridged indenyl-containing metallocenes are disclosed along with methods for making the metallocenes. Also disclosed are methods for using the metallocenes as polymerization catalysts. In addition, polymers resulting from such polymerizations are disclosed.

19 Claims, No Drawings

HIGH ACTIVITY ETHYLENE SELECTIVE METALLOCENES

This invention relates to organometallic compounds. More specifically, this invention relates to a specific type of metallocenes which can be referred to as unbridged metallocene of indenyl and pentamethylcyclopentadienyl. In another aspect, this invention relates to polymerization catalyst systems which contain such metallocenes. In still another aspect, this invention relates to a method for polymerizing olefins using such metallocenes and to the polymers resulting from such polymerizations.

BACKGROUND OF THE INVENTION

Since the discovery of ferrocene in 1951, a number of metallocenes have been prepared by the combination of compounds having the cyclopentadienyl structure with various transition metals. The term "cyclopentadienyl structure" as used herein refers to the following structure.

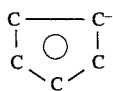

The term "cyclopentadiene-type compounds" as used herein refers to compounds containing the cyclopentadiene structure. Examples include unsubstituted cyclopentadiene, unsubstituted indene, unsubstituted fluorene, and substituted varieties of such compounds. Also included is tetrahydro indene.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and location of substitutions on cyclopentadienyl-type ligands has been found to affect the activity of the catalyst, the stereoselectivity of the catalyst, the stability of the catalyst, or other properties of the resulting polymer; however, the effects of various substituents is still largely an empirical matter, that is, experiments must be conducted in order determine just what effect a particular variation will have upon a particular type of cyclopentadienyl-type metallocene.

While there are references in the prior art which have envisioned various unbridged metallocenes, it is considered unlikely that all of the metallocenes within the broad disclosures of publications have actually been prepared and evaluated for their polymerization effects. For example, while U.S. Pat. No. 5,049,534 contains allegations regarding a wide range of both bridged and unbridged metallocenes, the only actual examples of unbridged metallocenes are those in which two identical cyclopentadienyl-type ligands are present.

An object of the present invention is to provide certain new indenyl-containing metallocenes. Still another object of the present invention is to provide polymerization catalysts employing the specific indenyl-type metallocenes. Still yet another object of the present invention is to provide processes for the polymerization of olefins using specific indenyl-type metallocene catalyst systems. Still yet another object of the present invention is to provide polymers produced using such indenyl-containing metallocene catalysts.

SUMMARY OF THE INVENTION

In accordance with the present invention, there are provided new unbridged metallocenes of the formula $(In)(Cp^*)MeQ_2$ wherein In is a substituted or unsubstituted indenyl radical; $Cp^*$ is a pentamethylcyclopentadienyl radical; Me is metal selected from the group consisting of Zr, Ti, and Hf; each Q is the same or different and is selected from the group consisting of hydrocarbyl or hydrocarbyloxy radicals having 1 to 20 carbon atoms, hydrogen, and halogens.

In accordance with another aspect of the present invention, there is provided a method for forming the specific indenyl-containing metallocenes comprising reacting an alkali metal salt of the selected indenyl with a transition metal compound of the formula $(Cp^*)MeQ_3$, in the presence of a non-halogenated solvent for the indenyl salt which solvent is non-coordinating with the transition metal halide.

In accordance with still another aspect of the present invention, there is provided a process for the polymerization of olefins comprising contacting said olefins under suitable reaction conditions with a catalyst system comprising the indenyl-containing metallocene as described above in combination with a suitable co-catalyst.

Still further in accordance with the present invention there is provide, the polymer products resulting from such polymerizations.

DETAILED DESCRIPTION OF THE INVENTION

The novel metallocenes provided in accordance with the present invention are unbridged, that is the indenyl ligand and the pentamethylcyclopentadienyl ligand that are bound to the metal are not bound to each other.

The substituents on the substituted indenyl can vary over a wide range. It is currently preferred that the substituents be hydrocarbyl or hydrocarbyoxy radicals having 1 to 10 carbon atoms. Particularly preferred substituents are alkyl and alkenyl radicals, especially alkenyl radicals having terminal olefinic unsaturation. In preferred embodiments the indenyl has 1 to 4 substituents.

The inventive metallocenes as well as related metallocenes can be prepare$_d$ by reacting an alkali metal salt of the indenyl compound with a suitable transition metal compound, for example $Cp^*ZrCl_3$, in a suitable solvent under suitable reaction conditions.

An especially preferred embodiment of the present invention involves carrying out the reaction of the indenyl-containing salt and the transition metal compound in the presence of a liquid diluent which is non-halogenated and non-coordinating toward the transition metal compound. Examples of such suitable liquid include hydrocarbons such as toluene, pentane, or hexane as well as non-cyclic ether compounds such as diethylether. It has been found that the use of such non-halogenated non-coordinating solvents generally allows one to obtain large amounts of substantially pure metallocenes in a more stable form, and often allows the reaction to be conducted under higher temperature conditions, than when dichloromethane is used as the diluent.

The formation of the alkali metal salt of the indenyl compound can be formed using generally any technique known in the art. For example, such can be prepared by reacting an alkali metal alkyl with the indene. The molar ratio of the alkali metal alkyl to the indene can vary;

generally however, the ratio would be in the range of about 0.5/1 to about 1.5/1, still more preferably about 1/1.

Typically, the alkali metal of the alkali metal alkyl would be selected from sodium, potassium, and lithium, and the alkyl group would have 1 to 8 carbon atoms, more preferably 1 to 4 carbon atoms. In the preferred embodiment if the indenyl salt is formed using tetrahydrofuran (THF) as the liquid solvent, the salt is isolated and substantially all of the THF is removed before the salt is contacted with the transition metal halide. The molar ratio of the indenyl salt to the transition metal compound can vary over a wide range depending upon the results desired. Typically, however, the indenyl salt is used at a molar ratio of the indenyl compound to the transition metal compound, i.e. Cp*MeQ$_3$, of about 1 to 1.

The resulting metallocene can be recovered and purified using conventional techniques known in the art such as filtration, extraction, crystallization, and re-crystallization. It is generally desirable to recover the metallocene in a form that is free of any substantial amount of by-product impurities. Accordingly, recrystallization and fractional crystallization to obtain relatively pure metallocenes is desireable. Dichloromethane has been found to be particularly useful for such recrystallizations. Since the stability of the various metallocenes varies, it is generally desirable to use the metallocenes soon after their preparation or at least to store the metallocene under conditions favoring their stability. For example the metallocenes can generally be stored in the dark at low temperature, i.e. below 0° C. in the absence of oxygen or water.

The resulting inventive indenyl-containing metallocenes can be used in combination with a suitable co-catalyst for the polymerization of olefinic monomers. In such processes the metallocene or the co-catalyst can be employed on a solid insoluble particulate support.

Examples of suitable co-catalysts include generally any of those co-catalysts which have in the past been employed in conjunction with transition metal containing metallocene olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, triisobutyl aluminum, diethyl aluminum chloride, diethyl aluminum hydride, and the like.

The currently most preferred co-catalyst is an aluminoxane. Such compounds include those compounds having repeating units of the formula

where R is an alkyl group generally having 1 to 5 carbon atoms. Aluminoxanes, also sometimes referred to as poly-(hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561, the disclosures of which ate incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The indenyl-containing metallocenes in combination with the aluminoxane co-catalyst can be used to polymerize olefins, especially alpha olefins having 2 to 12 carbon atoms. Often such polymerizations would be carried out in a homogeneous system in which the catalyst and co-catalyst were soluble; however, it is within the scope of the present invention to carry out the polymerizations in the presence of supported or insoluble particulate forms of the catalyst and/or co-catalyst. The catalyst is thus considered suitable for solution, slurry, or gas phase polymerization. It is within the scope of the invention to use a mixture of two or more of the inventive indenyl-containing metallocenes or a mixture of an inventive indenyl-containing metallocene with one or more other cyclopentadienyl-type metallocenes.

The indenyl-containing metallocenes when used with aluminoxane are particularly useful for the polymerization of ethylene in the presence or absence of other olefins. Examples of other olefins that might be present include mono-unsaturated aliphatic alpha-olefins having 3 to 10 carbon atoms. Examples of such olefins include propylene, butene-1, pentene-1, 3-methylbutene-1, hexene- 1, 4-methylpentene- 1, 3-methylpentene- 1, heptene- 1, octene- 1, decene- 1,4,4-dimethyl- 1-pentene, 4,4-diethyl- 1-hexene, 3-4-dimethyl-1-hexene, and the like and mixtures thereof. One of the characteristics of the inventive metallocene (indenyl) (pentamethylcyclopentadienyl) zirconium dichloride is that it is especially selective toward ethylene. Accordingly, ethylene feed which contains other olefins can often be used in the polymerization without the risk of the other olefins altering the desired end product characteristics of the polymer to the extent that they would with some other metallocenes.

The polymerizations can be carried out under a wide range of conditions depending upon the particular metallocene employed, and the results desired Examples of typical conditions under which the metallocenes can be used in the polymerization of olefins include conditions such as disclosed in U.S. Pat. Nos. 3,242,099; 4,892,851; and 4,530, 914; the disclosures of which are incorporated herein by reference. It is considered that generally any of the polymerization procedures used in the prior art with any transition metal based catalyst systems can be employed with the present inventive indenyl-containing metallocenes.

Generally the molar ratio of the aluminum in the aluminoxane to the transition metal in the metallocene would be in the range of about 0.1:1 to about 10:1 and more preferably about 5:1 to about 10: 1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about –60° C. to about 280° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer.

A further understanding of the present invention, its various aspects, objects and advantages will be provided by the following examples.

In the following examples, the metallocene preparations were carried out routinely using the Schlenk technique, with strict exclusion of air and moisture, by means of purified and dried inert gas.

The solvents which were used were dried over a sodium/potassium alloy or over phosphorus pentoxide in the case of dichloromethane and distilled in circulation equipment under an inert atmosphere. Toluene was additionally distilled over phosphorus pentoxide and dichloromethane was distilled over calcium hydride. Deuterated solvents for the NMR spectroscopy were stored over a molecular sieve.

The melting points of the organic compounds were determined in open tubes and those of the organometallic compounds were determined in closed tribes under nitrogen.

The organic compounds were characterized using a gas chromatograph with flame ionization detector and a fused silica column with helium as the carrier gas. The mass spectra was carried out using a mass spectrometer with electron impact ionization energy of 70 eV. The samples were introduced with the help of a direct inlet system or they were injected in the form of solutions.

Crystal structure investigations were conducted using a Mo-K alpha radiation ($\gamma=0.71073\text{Å}$) using a defractometer.

EXAMPLE I

About 2.4 mmol of fluorene was dissolved in 50 ml of ether and mixed with 1.5 ml of a 1.6 molar hexane solution of butyllithium at room temperature. After termination of the evolution of gas, an equal molar quantity of cyclopentadienyl zirconium trichloride was added and the mixture stirred for one hour. The solvent was then removed using the vacuum from a membrane pump. The remaining residue was extracted with toluene and filtered over sodium sulfate. The filtrate was concentrated by evaporation and brought to the point of crystallization. The resulting bright orange solid product was determined to be (fluorenyl) (cyclopentadienyl) zirconium dichloride, hereinafter referred to as Catalyst No. 27. $^1$H-NMR, $^{13}$C-NMR spectroscopy, mass spectrometer and decomposite temperatures were used to identify the compound. The mass spectrum indicated a molecular weight of 392. The material decomposed at 167° C. The $^1$H-NMR spectra showed a singlet resonance at about 6.08 which can be assigned to the protons of the CH ring and multiplet resonances in the regions of about 7.38–7.48 and about 7.57. A doublet was observed at about 8.13 and there was resonance at about 6.53.

EXAMPLE II

A process like that used in Example I was repeated by substituting either pentamethylcyclopentadienyl zirconium trichloride or pentamethylcyclopentadienyl hafnium trichloride for the cyclopentadienyl zirconium trichloride. This resulted in the following catalysts:

| Catalyst No. | Name |
| --- | --- |
| 63 | (fluorenyl)(pentamethylcyclopentadienyl) ZrCl$_2$ |
| 64 | (fluorenyl)(pentamethylcyclopentadienyl) HfCl |

EXAMPLE III

Using the same general technique as set forth in Example II, a number of additional metallocenes were prepared by substituting indenyl lithium for the fluorenyl lithium. Those reactions resulted in the following catalysts.

| Catalyst No. | Name |
| --- | --- |
| 83 | (indenyl) (pentamethylcyclopentadienyl) ZrCl$_2$ |
| 84 | (indenyl) (pentamethylcyclopentadienyl) HfCl$_2$ |

EXAMPLE IV

Using the same general technique as set forth in Example III, metallocenes were prepared by substituting either cyclopentadienyl titanium dichloride or cyclopentadienyl zirconium dichloride for the pentamethylcyclopentadienyl zirconium dichloride. Those reactions resulted in the following catalysts.

| Catalyst No. | Name |
| --- | --- |
| 81 | (indenyl) (cyclopentadienyl) TiCl$_2$ |
| 82 | (indenyl) (cyclopentadienyl) ZrCl$_2$ |

EXAMPLE VII

Ethylene Polymerization

The metallocenes prepared in the above examples were evaluated for the polymerization of ethylene. In each case, the metallocene was activated by dissolving in toluene and then mixing with a 30 Molar % toluene solution of methylaluminoxane. The formation of the active catalyst system solution expressed itself by a change in color.

The polymerizations were conducted by introducing 500 ml of pentane into a 1 liter autoclave with an internal temperature of 10° C. Then 5 ml of the catalyst system solution was introduced. After this, an ethylene pressure of 10 bar was applied and the reaction mixture was stirred for 1 hr at 10° C. The polymer which was obtained was filtered off and subsequently washed in each case with 300 ml of dilute caustic soda solution, water, and then acetone and liberated from the residual solvent by drying in a cabinet at 130° C. An comparable polymerization was conducted using the control catalyst bis(cyclopentadienyl) zirconium dichloride. The results of the polymerizations with the various metallocenes is summarized in Table I.

TABLE I

| | Polymerization Results | | |
| --- | --- | --- | --- |
| Catalyst | Amount [mg] | Polyethylene [g] | Activity [kg PE/g Metal-hr] |
| Cp$_2$ZrCl$_2$ | 2.0 | 40 | 64 |
| 27 | 2.0 | 80 | 172 |
| 63 | 2.1 | 55 | 137 |
| 64 | 2.4 | 44 | 39 |
| 81 | 2.5 | 23 | 146 |
| 83 | 0.5 | 75 | 685 |
| 84 | 1.6 | 40 | 70 |

The results show that the fluorenyl-containing Zr metallocenes 27 and 63 were more active than the bis(cyclopentadienyl) Zr metallocene control. Run 63 shows that the substitution of the pentamethylcyclopentadienyl ligand for the cyclopentadienyl ligand of catalyst 27 did not result in any improved activity for the catalyst. The indenyl counterparts of catalysts 63 and 54, i.e. catalysts 83 and 84, were however remarkably more active than the related fluorenyl-containing metallocenes.

That which is claimed is:

1. An unbridged metallocene of the formula (In)(Cp*)MeQ$_2$ wherein In is a or unsubstituted indenyl radical; Cp* is a pentamethylcyclopentadienyl radical; Me is a transition metal selected from the group consisting of titanium, zirconium, and hafnium; and each Q is the same or different and is selected from the group consisting of hydrocarbyl radicals having 1 to 12 carbon atoms, alkoxy radicals having 1 to 12 carbon atoms, aryloxy radicals having 6 to 12 carbon atoms, hydrogen, and halides.

2. A metallocene according to claim 1 wherein each Q is a halide.

3. A metallocene according to claim 2 wherein each Q is chloride.

4. A metallocene according to claim 3 wherein Me is zirconium.

5. A catalyst system useful for the polymerization of olefins comprising a metallocene as set forth in claim 1 and a organometallic cocatalyst.

6. A catalyst system according to claim 5 wherein the cocatalyst is selected from organoaluminum compounds.

7. A catalyst system according to claim 6 wherein methylaluminoxane is employed as cocatalyst.

8. A catalyst system according to claim 7 wherein Me of the metallocene is zirconium and each Q is chloride.

9. A catalyst system according to claim 6 wherein Me of the metallocene is zirconium and each Q is Cl.

10. A process for preparing a polyolefin comprising contacting ethylene under polymerization reaction conditions with a catalyst system as set forth in claim 5.

11. A process according to claim 10 wherein the cocatalyst of the catalyst system comprises an organoaluminum compound.

12. A process according to claim 11 wherein said cocatalyst an organoaluminoxane cocatalyst having repeating units of the formula

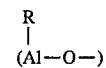

wherein each R is an alkyl radical having 1 to 5 carbon atoms is employed.

13. A process according to claim 12 wherein the metallocene of the Catalyst system is (indenyl) (pentamethylcyclopentadienyl) zirconium dichloride.

14. A process according to claim 13 conducted under particle form polymerization conditions.

15. A process according to claim 14 wherein said polymerization is conducted in a continuous loop reactor.

16. A process according to claim 15 wherein ethylene is polymerized.

17. A process according to claim 16 wherein another olefin having 4 to 10 carbon atoms is present during the polymerization.

18. A process according to claim 17 wherein the olefins present during the polymerization consists essentially of ethylene and 1-hexene.

19. A process according to claim 13 wherein ethylene is polymerized.

* * * * *

UNITED STATES PATENT AND TRADEMARK OFFICE
CERTIFICATE OF CORRECTION

PATENT NO. : 5,541,272

DATED : July 30, 1996

INVENTOR(S) : Michael Schmid et al

It is certified that error appears in the above-identified patent and that said Letters Patent is hereby corrected as shown below:

Column 7, line 3, after "a", please delete ---or---.

Signed and Sealed this

Twelfth Day of November, 1996

Attest:

BRUCE LEHMAN

Attesting Officer    Commissioner of Patents and Trademarks